US006342041B1

(12) United States Patent

Saint-Ramon et al.

(10) Patent No.: US 6,342,041 B1
(45) Date of Patent: Jan. 29, 2002

(54) DEVICE FOR DETECTING ESTRUS IN DAIRY COWS, INCLUDING A SUPPORT FOR A DETECTOR ENCLOSED IN A CASING AND EMITTING LUMINOUS SIGNALS

(76) Inventors: Jean-Gérard Saint-Ramon, 10 rue Clémenceau, 61300 L'Aigle; Michel Houdou, 19 boulevard Bédier, 49000 Angers, both of (FR)

(*) Notice: Subject to any disclaimer, the term of this patent is extended or adjusted under 35 U.S.C. 154(b) by 0 days.

(21) Appl. No.: 09/422,452

(22) Filed: Oct. 21, 1999

(30) Foreign Application Priority Data

Oct. 21, 1998 (FR) ........................................... 98 13196

(51) Int. Cl.[7] ................................................ A61B 10/00
(52) U.S. Cl. ....................................... 600/551; 119/174
(58) Field of Search ................................ 600/551, 587; 119/174

(56) References Cited

U.S. PATENT DOCUMENTS

| | | | | |
|---|---|---|---|---|
| 3,076,431 A | * | 2/1963 | Rule | 600/551 |
| 3,158,134 A | * | 11/1964 | Larson | 600/551 |
| 3,844,273 A | | 10/1974 | Polson | 600/551 |
| 3,942,475 A | | 3/1976 | Wassilieff et al. | 600/551 |
| 4,239,018 A | * | 12/1980 | Griffin et al. | 600/551 |
| 4,635,587 A | | 1/1987 | Leonardo | 600/551 |
| 4,846,106 A | * | 7/1989 | Leonardo | 600/551 |
| 4,895,165 A | * | 1/1990 | Blair | 600/551 |
| 5,111,799 A | | 5/1992 | Senger et al. | 600/551 |
| 5,542,431 A | | 8/1996 | Starzl et al. | 600/551 |
| 5,566,679 A | * | 10/1996 | Herriott | 600/551 |
| 5,839,390 A | * | 11/1998 | Meads | 119/174 |

FOREIGN PATENT DOCUMENTS

| | | |
|---|---|---|
| EP | 0 263 629 | 4/1988 |
| EP | 0 705 536 | 1/1998 |
| FR | 2432300 | 8/1979 |
| GB | 2027213 | 7/1979 |

* cited by examiner

*Primary Examiner*—Robert L. Nasser
*Assistant Examiner*—Charles Marmor, II

(57) ABSTRACT

A support for a casing containing a detector for detecting estrus in cows. The support comprises a natural fiber patch having a surface area in the range from approximately 0.04 $m^2$ to approximately 0.06 $m^2$ which supports a substantially rectangular case which receives the detector and is placed substantially at the center of the patch. The detector for detecting estrus in cows is housed in a casing supported by the support. The support comprises a baseplate capped by a cover.

24 Claims, 3 Drawing Sheets

FIG. 6
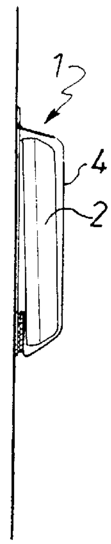
FIG. 5
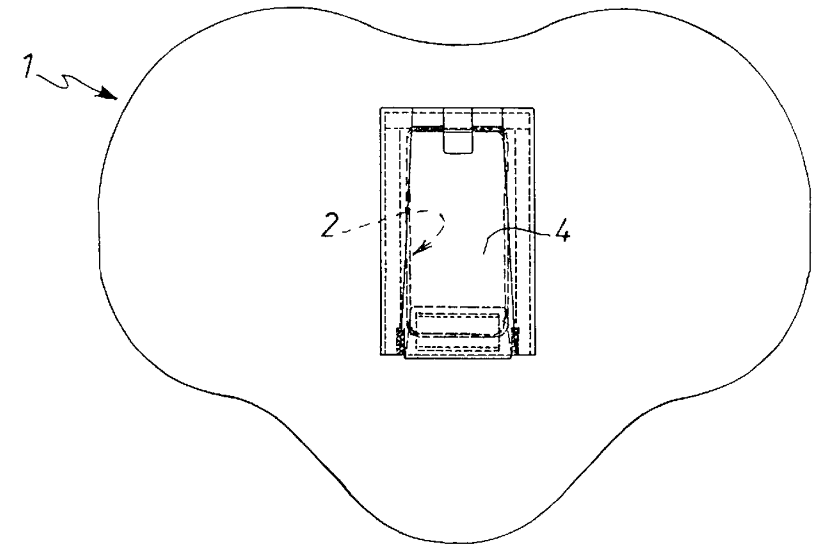
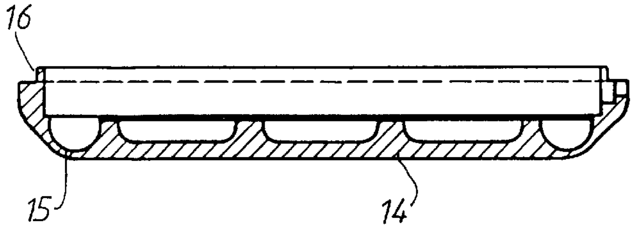
FIG 8
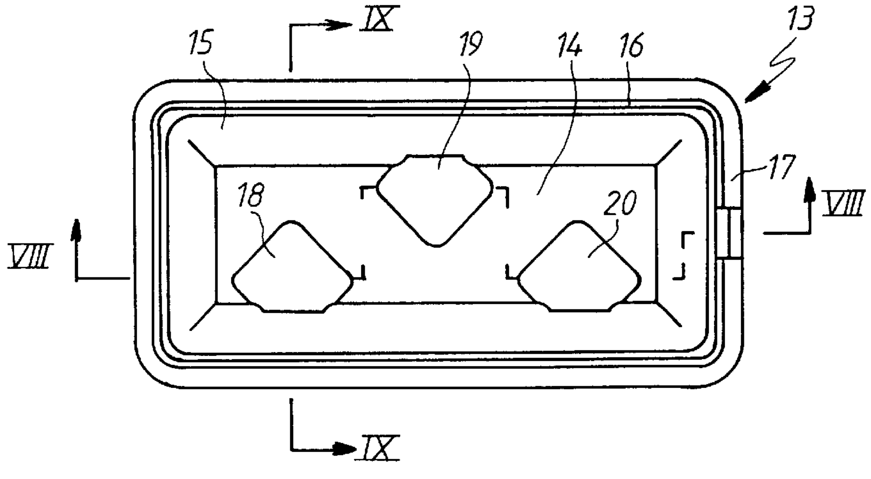
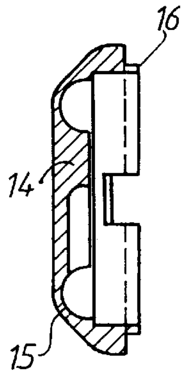
FIG 7
FIG 9

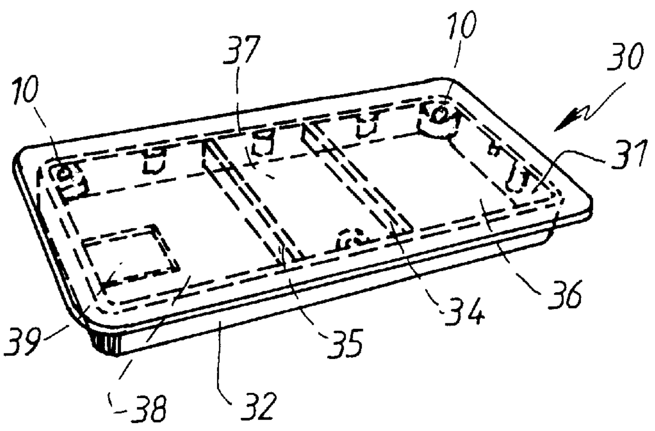
FIG 10
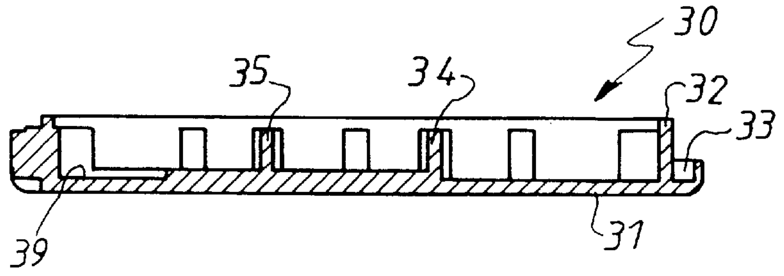
FIG 12
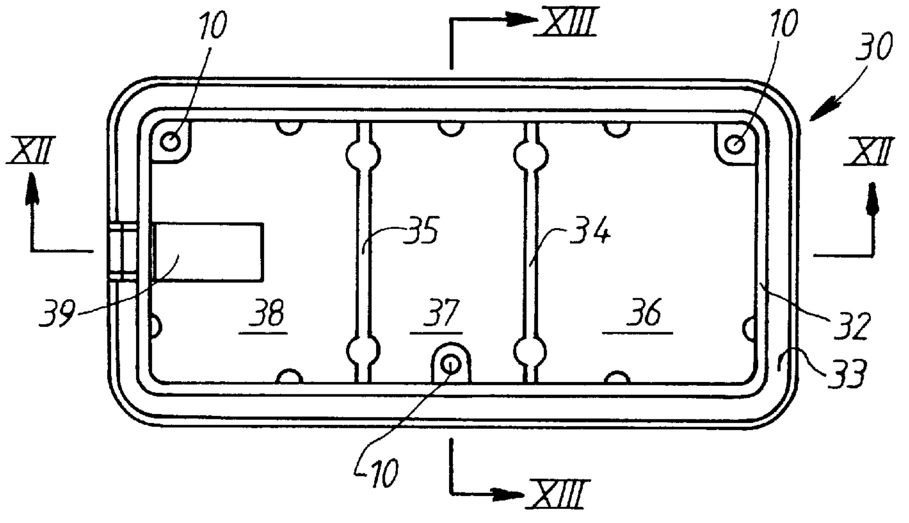
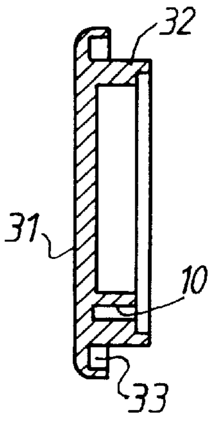
FIG 11
FIG 13

DEVICE FOR DETECTING ESTRUS IN DAIRY COWS, INCLUDING A SUPPORT FOR A DETECTOR ENCLOSED IN A CASING AND EMITTING LUMINOUS SIGNALS

BACKGROUND OF THE INVENTION

1. Field of the invention

The present invention concerns a device for detecting estrus in dairy cows. The invention is more particularly concerned with a device of this kind comprising a support for a detector for detecting estrus in cows which is enclosed in a casing and emits luminous signals.

The invention therefore relates to a support for a detector for detecting estrus in cows, a casing for a detector for detecting estrus in cows adapted to be supported by a support of the above kind and the combination of the support and the detector in its casing.

2. Description of the prior art

Every year millions of cows are artificially inseminated worldwide, a great many in France.

It is necessary to detect estrus in animals with the greatest possible precision, especially in dairy cows.

There are many devices for indicating estrus in animals, especially in dairy cows. FR 2 432 300 describes a device for indicating the periods when mammals are in heat, especially cows, by determining the temperature of the milk from the cow. EP 0 705 536 describes a movement sensor depending on the position of the cows.

When they are in estrus, cows are more active. In particular they have a tendency to mount each other.

U.S. Pat. No. 3,844,273, U.S. Pat. No. 5,542,431 and EP-A-0 263 629 describe a device comprising a detector on a support worn by the cow, habitually fixed to the crupper of the animal.

All the prior art devices have drawbacks.

The devices frequently become detached from the animal to which they have been fixed when they mount each other, leading to a significant loss for the farmer.

U.S. Pat. No. 5,111,799 describes a device for detecting estrus in cows and other animals which is implanted under the skin of the cow. A device of this kind remains f fixed to the animal but cannot be conveniently examined or recovered.

Cows also have different physiognomies and these vary considerably from one breed to another. Prior art detector devices do not take account of these differences and are designed only for a specific breed.

An object of the present invention is to propose a device for detecting estrus in cows which remains fixed to the crupper of the animals when they mount each other.

Another object of the present invention is to provide a device for detecting estrus in cows that can be used with any breed of cow.

A further object of the present invention is to provide a device whose detector can easily be examined and recovered.

Other objects and advantages of the invention will become apparent from reading the following description.

SUMMARY OF THE INVENTION

The present invention addresses the above objects and provides a support for a detector comprising a casing containing means for detecting estrus in cows, the support comprising a natural fiber patch having a surface area in the range from approximately 0.04 $m^2$ to approximately 0.06 $m^2$ adapted to support a substantially rectangular case adapted to receive the detector and placed substantially at the center of the patch.

In a preferred embodiment of the invention the patch is substantially heart-shaped.

The overall width of the support is advantageously in the range from approximately 0.15 m to approximately 0.3 m and its overall height is advantageously in the range from approximately 0.15 m to approximately 0.25 m.

The case generally includes self-gripping closure means with a lug.

The case is usually made from synthetic fibers, for example polyester fibers, such as high-strength polyester fibers.

The case can have one or two observation openings.

In another embodiment of the invention the upper part of the case is sufficiently transparent to enable luminous signals emitted by the detector to be detected and counted.

The support is advantageously made of natural fibers. Crash is a particularly appropriate material for the patch. Other materials can be used, however.

The case can be an integral part of the patch but preferably includes a base which is sewn to the patch.

Optionally, the support includes straps to secure it to the back of a cow.

To facilitate the position finding of the cows, the patch can have a fluorescent color.

The present invention also provides a detector casing adapted to be supported by a support as defined above and to contain means for detecting estrus in cows and comprising a baseplate capped by a cover.

The baseplate has a back wall with two areas of different thickness, namely a relatively thick central area constituting a beam and a thinner peripheral area around the beam, the peripheral area being flanked by a rim on top of which is a peripheral lip, the beam having three housings adapted to receive a sensing system based on pressure sensors.

According to one feature of the invention, optionally combined with the previous feature, the cover comprises ribs and a cover plate carrying a skirt surrounded by a peripheral groove, which skirt and ribs constitute three compartments, namely a first compartment adapted to receive an electrical power supply, a second compartment adapted to receive means for analyzing and processing a signal and a third compartment having a housing adapted to receive a lens for optimum diffusion of luminous signals.

The baseplate and the cover are usually assembled by gluing the peripheral lip of the baseplate into the peripheral groove on the cover.

For relative positioning of the baseplate and the cover and for holding them while the glue sets, pins on the baseplate are clipped into housings on the cover.

The glue is a two-component polyurethane glue, for example.

The cover of the casing is usually made of polycarbonate, generally transparent polycarbonate.

The baseplate, which is generally substantially pyramid-shaped, is advantageously injection molded from flexible polyurethane.

The cover is generally substantially rectangular and the base of the baseplate is also generally substantially rectangular.

The present invention therefore provides a device for detecting estrus in dairy cows, the device comprising a support including a casing adapted to receive means for detecting estrus in cows, the detector means emitting luminous signals, being enclosed in the casing and inserted in the case, the support and the casing being as defined above.

BRIEF DESCRIPTION OF THE DRAWINGS

The description will be better understood with reference to the accompanying drawings, in which:

FIG. 5 is a diagrammatic top view of the support of the invention comprising the detector inside the case (or pouch) with the closure lug closed.

FIG. 6 is a (left-hand) side view of FIG. 5.

FIG. 7 is a diagrammatic top view of a baseplate of a casing in accordance with the invention.

FIG. 8 is a view in section taken along the line VIII—VIII in FIG. 7.

FIG. 9 is a view in section taken along the line IX in FIG. 7.

FIG. 10 is a diagrammatic perspective view of the cover of a case in accordance with the invention.

FIG. 11 is a diagrammatic top view of a cover of a case in accordance with the invention.

FIG. 12 is a view in section taken along the line XII in FIG. 11.

FIG. 13 is a view in section taken along the line XIII in FIG. 11.

DETAILED DESCRIPTION OF THE PREFERRED EMBODIMENT

Figure 1:
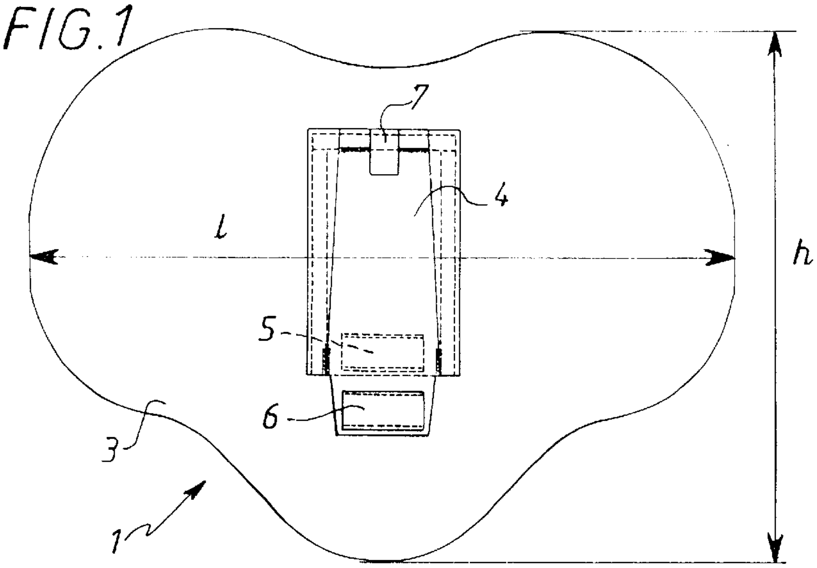
FIG. 1 is a diagrammatic top view of the support of the invention.
Figure 2:
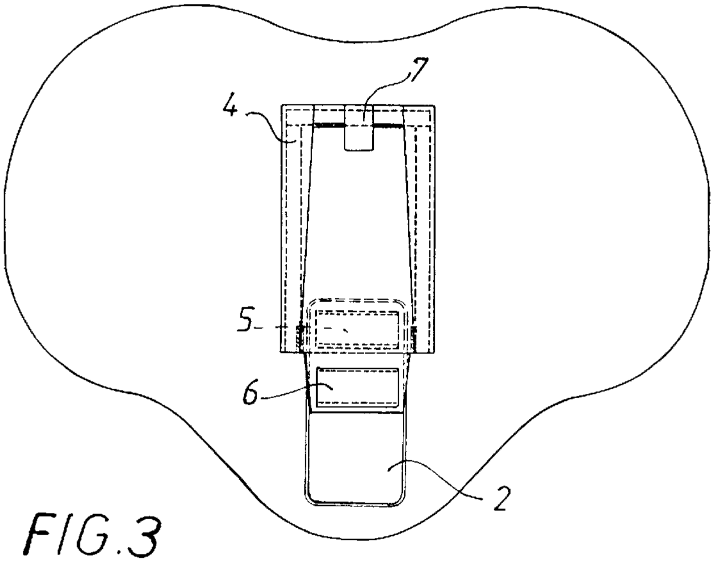
FIG. 2 is a diagrammatic top view of the support of the invention on starting to insert the detector.
Figure 4:
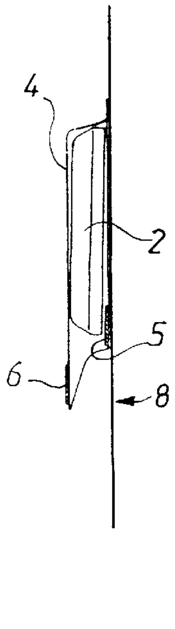
FIG. 4 is a (right-hand) side view of FIG. 3.
Figure 3:
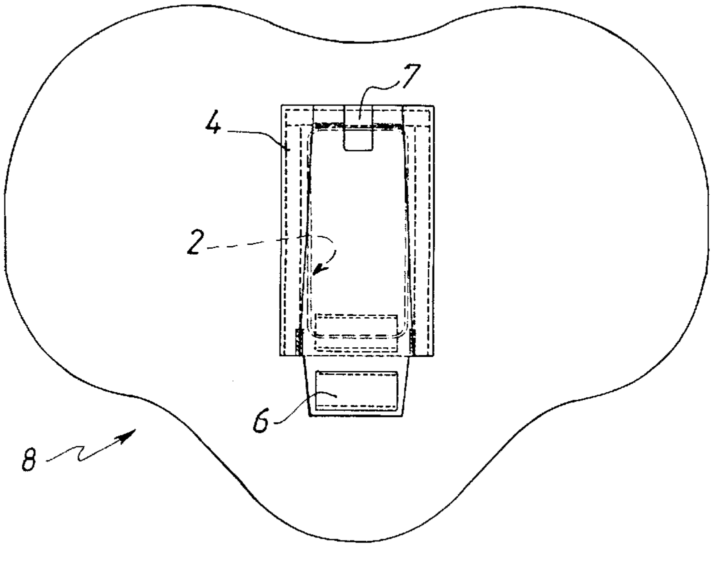
FIG. 3 is a diagrammatic top view of a support assembly comprising a detector inserted in a case with the closure lug open.

The heart-shaped support 1 for a detector 2 for detecting estrus in cows comprises a natural fiber patch 3 supporting a rectangular case 4 adapted to receive said detector placed at the center of the patch.

The overall width l of the support is in the range from approximately 0.15 m to approximately 0.3 m and its overall height h is in the range from approximately 0.15 m to approximately 0.25 m.

The case 4 includes self-gripping closure means 5 with a lug 6.

The case includes an observation opening 7.

The case 4 includes a base which is sewn to the patch.

The casing has a baseplate 13 capped by a cover 30. The substantially rectangular pyramid-shaped baseplate 13 has a bottom wall with two areas of different thickness, a relatively thick central area 14 constituting a beam and a thinner peripheral area 15 surrounding said beam 14. The peripheral area is flanked by a rim 17 on top of which is a peripheral lip 16. The beam 14 has three housings 18, 19 and 20 adapted to receive a sensing system based on pressure sensors.

The rectangular cover 30 comprises a cover plate 31 with a skirt 32 surrounded by a peripheral groove 33 and ribs 34, 35 which, in conjunction with said skirt 32 constitute three compartments 36, 37 and 38. The first compartment 36 receives the electrical power supply, the second compartment 37 receives the means for analyzing and processing a signal and the third compartment 38 has a housing 39 which receives a lens (not shown) for optimum diffusion of luminous signals.

The peripheral groove 33 provides a reservoir of glue for assembling the baseplate 13 and the cover 30.

Pins on the baseplate 13 clip into housings 10 on the cover 30 to assure relative positioning of the baseplate 13 and the cover 30 and to hold them while the glue sets.

The assembly 8 comprises the support 1 including a detector 2 of estrus in cows which emits luminous signals, is enclosed in the casing described above and inserted in the case 4.

When cows mount each other, the pressure sensors integrated into the detector register a pressure and the detector emits luminous signals.

The detector 2 is inserted into the case 4, with the baseplate against the base sewn to the patch, so that the indicator light can be observed. The closure 5 is closed by means of the lug 6.

The resulting device 8 is then stuck to the crupper of the animal, as close as possible to its tail.

An appropriate glue is sprayed onto the back of the support, i.e. the side opposite the case 4. This operation is preferably carried out at ambient temperature, provided that this is at least 10° C. The glue is then allowed to dry to that it no longer adheres to the finger.

The hide of the animal must be clean and dry. To this end it is necessary to brush the crupper of the animal and if necessary to cut its fur so that its length does not exceed about 1 cm.

The support to which the glue has been applied is placed as close as possible to the tail of the animal, centered relative to its spine. A layer of glue is sprayed onto the back of the animal. The support is then placed where the glue has been deposited and pressure is applied, for example with a brush, with the emphasis on the edges of the support.

The detector is then pressed to verify that it is working. The indicator lamp should light.

The skilled person will understand that although the invention has been described and shown by way of a particular embodiment, many variants can be envisaged that fall within the scope of the invention as defined by the accompanying claims.

What is claimed is:

1. A support supporting a detector comprising a casing containing means emitting luminous signals for detecting estrus in cows, said support comprising a natural fiber patch having a surface area in the range from approximately 0.04 $m^2$ to approximately 0.06 $m^2$, say patch supporting a substantially rectangular case adapted to receive said detector placed substantially at the center of said patch.

2. The support claimed in claim 1, wherein said patch is substantially heart-shaped.

3. The support claimed in claim 1, wherein the overall width of the support is in the range from approximately 0.15 m to approximately 0.3 m and the overall height of the support is in the range from approximately 0.15 m to approximately 0.25 m.

4. The support claimed in claim 1, wherein said case includes a self-gripping closure device with a lug.

5. The support claimed in claim 1, wherein said case is made from synthetic fibers.

6. The support claimed in claim 5, wherein said synthetic fibers are polyester fibers.

7. The support claimed in claim 1, wherein said case has an observation opening.

8. The support claimed in claim 1, wherein said case has two observation openings.

9. The support claimed in claim 1, wherein an upper part of said case is sufficiently transparent to enable luminous signals emitted by said detector to be detected and counted.

10. The support claimed in claim 1, wherein said natural fibers constituting said patch are crash.

11. The support claimed in claim 1, wherein said case includes a base and said base is sewn to said patch.

12. The support claimed in claim 1, wherein said support includes straps to secure said support to the back of a cow.

13. The support claimed in claim 1, wherein said patch s a fluorescent color.

14. A detector casing supported by a support for a detector, said detector casing comprising a casing for containing means for detecting estrus in cows, said support comprising a natural fiber patch having a surface area in the range from approximately 0.04 $m^2$ to approximately 0.06 $m^2$ supporting a substantially rectangular case adapted to receive the detector placed substantially at the center of said patch to contain means for detecting estrus in cows, said casing comprising a baseplate capped by a cover.

15. The casing claimed in claim 14, wherein said baseplate has a back wall with two areas of different thickness, namely a relatively thick central area constituting a beam and a thinner peripheral area around said beam, said peripheral area being flanked by a rim on top of which is a peripheral lip, said beam having three housings adapted to receive a sensing system based on pressure sensors.

16. The casing claimed in claim 14, wherein said cover comprises a cover plate carrying ribs and a skirt surrounded by a peripheral groove, which skirt and ribs constitute three compartments, namely a first compartment adapted to receive an electrical power supply, a second compartment adapted to receive means for analyzing and processing a signal and a third compartment having a housing adapted to receive a lens for optimum diffusion of luminous signals.

17. The casing claimed in claim 14, wherein said baseplate and said cover are assembled by gluing said peripheral lip of said baseplate into said peripheral groove on said cover.

18. The casing claimed in claim 14, wherein, for relative positioning of said baseplate and said cover and for holding them while said glue sets, pins on said baseplate are clipped into housings on said cover.

19. The casing claimed in claim 17, wherein said glue is a two-component polyurethane glue.

20. The casing claimed in claim 14, wherein said cover is made of polycarbonate.

21. The casing claimed in claim 20, wherein said polycarbonate is transparent.

22. The casing claimed in claim 14, wherein said baseplate is injection molded from flexible polyurethane.

23. The casing claimed in claim 14, wherein said baseplate is substantially pyramid-shaped.

24. The casing claimed in claim 14, wherein said cover is substantially rectangular and the base of said baseplate is substantially rectangular.

* * * * *